United States Patent [19]
Groenke

[11] Patent Number: 5,727,616
[45] Date of Patent: Mar. 17, 1998

[54] ELASTOMERIC HEAT EXCHANGER BED

[75] Inventor: Allen W. Groenke, Bloomington, Minn.

[73] Assignee: EdenTec, Eden Prairie, Minn.

[21] Appl. No.: 549,274

[22] Filed: Oct. 27, 1995

[51] Int. Cl.$^6$ .............................. F28D 19/00; A62B 7/00
[52] U.S. Cl. .................... 165/4; 55/267; 96/126; 96/146; 128/201.13; 128/204.13; 165/10
[58] Field of Search ............... 55/267, 278; 95/117, 95/121, 288, 902; 96/108, 147, 154, 126, 123, 146; 128/201.13, 203.16, 204.13; 165/111, 4, 10

[56] References Cited

U.S. PATENT DOCUMENTS

| | | | |
|---|---|---|---|
| 453,677 | 6/1891 | Upjohn | 128/204.13 |
| 2,196,021 | 4/1940 | Merrill | 96/154 |
| 2,610,038 | 9/1952 | Phillips | 257/245 |
| 3,183,963 | 5/1965 | Mondt | 165/10 |
| 3,626,671 | 12/1971 | Ebeling, Jr. | 96/126 |
| 3,747,598 | 7/1973 | Cowans | 128/142 |
| 4,054,980 | 10/1977 | Roma | 29/157.3 |
| 4,069,028 | 1/1978 | Brown | 62/3 |
| 4,124,478 | 11/1978 | Tsien et al. | 204/255 |
| 4,172,164 | 10/1979 | Meyer et al. | 428/72 |
| 4,200,094 | 4/1980 | Gedeon et al. | 128/201.13 |
| 4,201,206 | 5/1980 | Kuehn et al. | 165/10 |
| 4,234,326 | 11/1980 | Bailey et al. | 96/154 |
| 4,258,784 | 3/1981 | Perry et al. | 165/166 |
| 4,294,242 | 10/1981 | Cowans | 128/201.13 |
| 4,325,365 | 4/1982 | Barbuto | 128/201.13 |
| 4,332,135 | 6/1982 | Barclay et al. | 62/3 |
| 4,411,310 | 10/1983 | Perry et al. | 165/166 |
| 4,432,409 | 2/1984 | Steele | 165/8 |
| 4,512,392 | 4/1985 | van Ee et al. | 165/54 |
| 4,577,678 | 3/1986 | Franenfeld et al. | 165/10 |
| 4,733,718 | 3/1988 | Schikowsky et al. | 165/4 |
| 4,744,414 | 5/1988 | Schon | 165/167 |
| 4,801,308 | 1/1989 | Keefer | 96/126 |
| 4,817,708 | 4/1989 | Ono et al. | 165/54 |
| 4,858,685 | 8/1989 | Szucs et al. | 165/166 |
| 4,875,520 | 10/1989 | Steele et al. | 165/10 |
| 4,955,435 | 9/1990 | Shuster et al. | 165/170 |
| 5,022,394 | 6/1991 | Chmielinski | 128/207.14 |
| 5,035,236 | 7/1991 | Kanegaonkar | 128/201.13 |
| 5,038,775 | 8/1991 | Maruscak et al. | 128/205.27 |
| 5,113,666 | 5/1992 | Parrish et al. | 96/154 |
| 5,308,703 | 5/1994 | Tsujimoto et al. | 96/154 |
| 5,320,096 | 6/1994 | Hans | 128/205.29 |
| 5,339,653 | 8/1994 | DeGregoria | 62/467 |
| 5,462,048 | 10/1995 | Lambert et al. | 128/201.13 |

OTHER PUBLICATIONS

K. Prasad, M.D. et al., "Heat & Moisture Exchangers (HME's): Physics, Function and Efficacy–How Do they Work? Are They All Created Equal?", Beth Israel Medical Center, Department of Anesthesiology, date prior to or even with Oct. 27, 1995, 4 pages.

R. Branson et al., "Humidification in the Intensive Care Unit", *Clinical Investigations in Critical Care*, Dec., 1993, 7 pages.

I. Cohen, M.D. et al., "Endotracheal Tube Occlusion Associated with the Use of Heat and Moisture Exchangers in the Intensive Care Unit," *Critical Care Medicine*, vol. 16, No. 3, Mar., 1988, 3 pages.

R. Branson et al., "Laboratory Evaluation of Moisture Output of Seven Airway Heat and Moisture Exchangers," *Respiratory Care*, vol. 32, No. 9, Sep., 1987, 3 pages.

W. Pratt, Jr. et al., "A Continuous Demagnetization Refrigerator Operating Near 2K and a Study of Magnetic Refrigerants," *Cryogenics*, Dec., 1977, 3 pages.

G.V. Brown, "Magnetic Heat Pumping Near Room Temperature," *Journal of Applied Physics*, vol. 47, No. 8, Aug., 1976, pp. 3673–3680.

(List continued on next page.)

*Primary Examiner*—C. Scott Bushey
*Attorney, Agent, or Firm*—Nawrocki, Rooney & Sivertson

[57] ABSTRACT

A heat exchanger bed including a plurality of elastomeric sheets. The sheets have a peripheral edge and a center. The sheets also have an opening therethrough proximate the center. The sheets are stacked one next to another in a stack. At least one sheet spacer is disposed between adjacent sheets of the stack. The center openings of adjacent sheets are aligned to define a passage through the stack.

5 Claims, 1 Drawing Sheet

OTHER PUBLICATIONS

A.J. DeGregoria et al., "Test Results of an Active Magnetic Regenerate Refrigerator," *Advances in Cryogenic Engineering*, vol. 37, Part B., 1992, pp. 875–882.

R. Farris, "Rubber Heat Engines, Analyses and Theroy," *Polymer Engineering and Science*, vol. 17, No. 10, Oct. 1977, pp. 737–744.

L. Treloar, *The Physics of Rubber Elasticity*, Second Edition, Oxford at the Clarendon Press, 1956, 3 pages.

R. Hay, M.D. et al., "Efficacy of a New Hygroscopic Condenser Humidifier," *Critical Care Medicine*, vol. 10, No. 1, Jan., 1982, 5 pages.

C. Martin, M.D. et al., "Performance Evaluation of Three Vaporizing Humidifiers and Two Heat and Moisture Exchangers in Patients with Minute Ventilation>10L/Min.," *Chest*, Sainte Marguerite Hospital, University of Marseilles, Marseilles Medical School, Nov., 1992, pp. 1347–1350.

B. Eckerbom et al., "Performance Evaluation of Six Heat and Moisture Exchangers According to the Draft International Standard (ISO/DIS 9360)," *Acta Anaesthesiol Scand*, vol. 34, 1990, pp. 404–408.

P. Bickler, M.D., et al. "Efficiency of Airway Heat and Moisture Exchangers in Anesthetized Human," *Anesth Analq*, vol. 71, 1990, pp. 415–418.

T. Sottiaux, M.D. et al., "Comparative Evaluation of Three Heat and Moisture Exchangers During Short–Term Postoperative Mechanical Ventilation," *Chest*, Jul., 1993, pp. 220–224.

ELASTOMERIC HEAT EXCHANGER BED

BACKGROUND OF THE INVENTION

The present invention pertains generally to the field of heat exchangers and, in particular, to elastomeric heat exchanger beds used in respiratory therapies.

Warming and humidification of expired gases are generally necessary when therapeutic respiratory devices are used. The temperature and humidity of the gas introduced into a patient from a therapeutic respiratory device should match the inspiratory conditions occurring at the point the gas enters the patient's respiratory system. If the level of humidity is less than this level, a humidity deficit may be produced. If the level of humidity is greater than this, fluid overload and patient discomfort may result. High or low inspired gas temperatures can undesirably elevate or depress a patient's body temperature. Ideally, gases delivered through the mouth should be heated and humidified to room conditions. For example, gases delivered to a patient's nose through a mask should preferably be at a room temperature of 20° C. and a relative humidity of 50%.

Devices for warming inspired gases may be passive and/or active. Such devices have included polymer heat exchanger beds. In a passive device, the bed merely passively absorbs or releases heat. Active devices depend upon conversion of one type of energy to heat. In active devices, mechanical energy is added to the heat exchanger system. In the vapor compression cycle commonly used in refrigerators and air conditioners, for example, mechanical energy is added to the system to compress a refrigeration fluid.

In addition to the vapor compression cycle, the thermoelastic effect can be used for heating or cooling. In using the thermoelastic effect, certain elastomers can be used in active heat exchanger beds rather than refrigeration fluid. In accordance with the thermoelastic effect, an elastomer such as rubber warms upon stretching and cools upon relaxing. The thermoelastic effect can be utilized in a refrigerator, air conditioner and/or heat pump.

SUMMARY OF THE INVENTION

The present invention pertains to heat exchanger beds for passive and/or active heat exchange. The heat exchanger bed of the present invention can be used in respiratory therapies or in unrelated applications requiring heating and cooling.

The heat exchanger bed of the present invention includes at least one core member and a plurality of elastomeric sheets. The sheets can be made from a polymer having a high heat capacity. Each sheet has an opening therethrough and a first peripheral edge and an oppositely disposed second peripheral edge. The bed includes a plurality of sheet spacers disposed around a passage, wherein at least one spacer is disposed between adjacent sheets to maintain flow channels between the sheets. The core member extends through the passage such that a first portion of each sheet proximate the first edge is stressed in tension. A second portion of each sheet proximate the second edge is stressed in tension greater than the first portion near the first edge.

The sheets can include a desiccant, if significant moisture retention is desired. Typical desiccants may include calcium chloride, activated alumina, silica gel or others. The preferred desiccant is molecular sieves.

The spacers can be elongate members extending between the first and second peripheral edges. In one embodiment, there can be at least two spacers between each sheet. One spacer of the at least two spacers can be aligned at approximately 180° around the passage from a first spacer of the at least two spacers.

The heat exchanger bed can be used in passive heat exchange devices such as heat and moisture exchangers which are well known in the art. In active devices, the bed can be used by stressing the elastomeric sheets in tension. If two core members extend through the passage, the stack can be moved from a first position to a second position wherein the sheets are under greater stress than in the first position. This can be accomplished by moving the two core members from a first location to a second location in which the two core members are spaced further apart than in the first location.

DETAILED DESCRIPTION OF THE INVENTION

Figure 1:
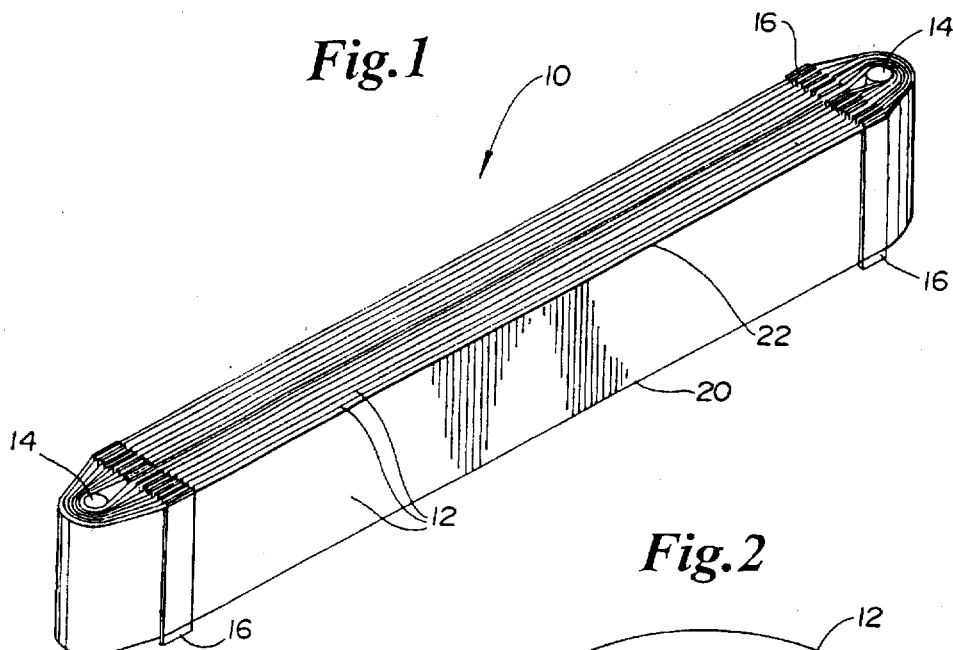
FIG. 1 is a perspective view of a heat exchanger bed in accordance with the present invention including elastomeric sheets under tension.

Referring now to the drawings wherein like reference numerals refer to like elements throughout the several views, FIG. 1 shows an elastomeric heat exchanger bed in accordance with the present invention generally referred to by the numeral 10. As shown, bed 10 includes a plurality of elastomeric sheets 12 stretched in tension around two core members 14. Each sheet is spaced from an adjacent sheet by at least one spacer 16. As shown in FIG. 1, however, each sheet is spaced by four spacers, two proximate each core member 14.

Figure 2:
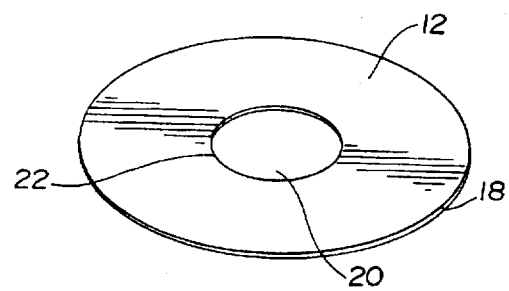
FIG. 2 is a perspective view of an elastomeric sheet of the heat exchanger bed in accordance with the present invention.

FIG. 2 is a view of an elastomeric sheet 12 prior to being placed under stress between core members 14. Sheet 12 includes a peripheral edge 18 and a generally centrally located opening 20 having a peripheral edge 22. The peripheral edges 18 and 22 lie generally in the same plane. Elastomeric sheets 12 are preferably formed from a polymer such as polyurethane. In one embodiment of sheet 12, it has an unstressed outside diameter of four inches and a thickness of 0.005".

Figure 3:
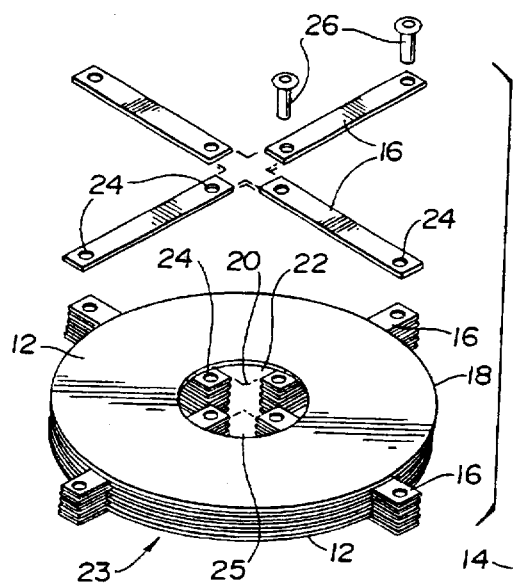
FIG. 3 is a view of the heat exchanger bed in accordance with the present invention before the sheets are placed under tension.

FIG. 3 is an exploded view of a stack 23 of elastomeric sheets 12 as shown in FIG. 2 having four spacers 16 disposed between adjacent sheets 12. Sheets 12 are stacked such that openings 20 are aligned to form a passage 25. As shown in FIG. 3, spacers 16 are elongate in shape and include openings 24 through opposite ends of each spacer. Spacers 16 preferably extend across sheets 12 from opening 20 to peripheral edge 18.

As stack 23 is assembled, spacers 16 can be placed on one elastomeric sheet 12 four at a time as shown in FIG. 3, or as a single spacer which is later divided into four spacers. For example, the lines shown extending between the adjacent ends of spacers 16 shown above stack 23 in FIG. 3 can be considered to be material which connects four spacers 16 together but is later removed. After a desired number of elastomeric sheets 12 are placed to form stack 23, opposite ends of spacers 16 may be joined by fasteners such as rivets 26 to retain spacer 16 between sheets 12. It should be understood that other means of fastenings ends of spacer 16 such as heat welding can also be used in accordance with the present invention. The number of elastomeric sheets 12 placed in stack 23 depends upon what application heat exchanger bed 10 will be placed in and the specific elastomeric material used to form sheets 12.

Figure 4:
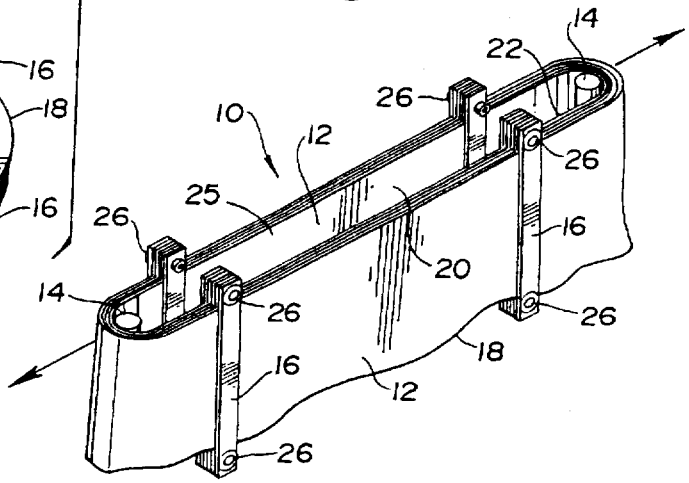
FIG. 4 is a view of a heat exchanger bed wherein the sheets are being placed under tension.

FIG. 4 is a view of heat exchanger bed 10 as it is transitioned from the position of stack 23. As shown by the arrows in FIG. 4, core members 14 extending through passage 25 are being drawn in opposite directions to place a portion of elastomeric sheets 12 proximate edge 22 in tension. Edges 18 and 22 are no longer in the same plane. While this happens, a portion of sheets 12 proximate peripheral edge 18 takes on a rippled shape. Continued separation of core members 14 results in a configuration as shown in FIG. 1 where both portions of sheets 12 proximate peripheral edges 18 and 22 respectively are in tension (note that in FIG. 1 the ends of spacer 16 and rivets 22 are not shown for clarity). It can be appreciated that the bed 10 of FIG. 1 can be placed under greater or lesser stress by moving core members 14 further apart or closer together respectively.

In use, heat exchanger bed 10 of the present invention can be used in devices for heating or cooling, such as a device for heating inspired gases. Devices for heating inspired gases may be passive and/or active. In a passive device, bed 10 passively absorbs or releases heat. In an active device, one type of energy, for example, mechanical energy, is converted to heat. This would also be the case in the vapor compression cycle commonly used in refrigerators and air conditioners. However, with respect to elastomeric heat exchanger bed 10, the thermoelastic effect can be used for heating or cooling.

As known in the art, certain elastomers can be used in heat exchanger beds rather than refrigeration fluid as used in a vapor compression cycle. In accordance with the thermoelastic effect, an elastomer heat exchanger bed, such as bed 10, warms upon stretching and cools upon relaxing. By appropriately channeling air through the bed while it is either being stretched or being relaxed, the bed can be utilized in a refrigerator, air conditioner and/or heat pump.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A heat exchanger bed, comprising:
   a plurality of elastomeric sheets, the sheets having a peripheral edge and a center, and the sheets having an opening therethrough proximate the center; and
   a plurality of sheet spacers, wherein the sheets are stacked one next to another in a stack with at least one spacer disposed between adjacent sheets in the stack, and the center openings of adjacent sheets being aligned to define a passage through the stack, wherein the spacer is an elongate member extending between the opening and the peripheral edge.

2. The heat exchanger bed in accordance with claim 1, wherein the sheets have a generally circular peripheral edge.

3. The heat exchanger bed in accordance with claim 2, wherein the opening is generally circular.

4. The heat exchanger bed in accordance with claim 1, wherein there are at least two spacers between each sheet and one spacer of the at least two spacers is aligned at approximately 180° around the center from a first spacer of the at least two spacers.

5. A heat exchanger bed in accordance with claim 4, wherein the spacers are disposed between the sheets in such a manner as to define with adjacent sheets two channels between the passage and the peripheral edge.

* * * * *